United States Patent
Liu

(10) Patent No.: US 9,955,729 B2
(45) Date of Patent: *May 1, 2018

(54) ELECTRONIC CIGARETTE

(71) Applicant: KIMREE HI-TECH INC., Road Town, Tortola (VG)

(72) Inventor: Qiuming Liu, Guangdong (CN)

(73) Assignee: HUIZHOU KIMREE TECHNOLOGY CO., LTD. SHENZHEN BRANCH, Shenzhen, Guangdong (CN)

( * ) Notice: Subject to any disclaimer, the term of this patent is extended or adjusted under 35 U.S.C. 154(b) by 523 days.

This patent is subject to a terminal disclaimer.

(21) Appl. No.: 14/636,641

(22) Filed: Mar. 3, 2015

(65) Prior Publication Data

US 2015/0289567 A1  Oct. 15, 2015

Related U.S. Application Data

(63) Continuation of application No. PCT/CN2014/075361, filed on Apr. 15, 2014.

(51) Int. Cl.
*A24F 13/00* (2006.01)
*A24F 11/00* (2006.01)
(Continued)

(52) U.S. Cl.
CPC .......... *A24F 47/008* (2013.01); *A61M 11/042* (2014.02); *A61M 15/0035* (2014.02)

(58) Field of Classification Search
CPC .................. A61M 11/044; A61M 11/042; A61M 11/041; A61M 15/0035; A61M 15/06;
(Continued)

(56) References Cited

U.S. PATENT DOCUMENTS 4,735,217 A * 4/1988 Gerth ............... A24F 47/008
128/203.17
2013/0192618 A1 8/2013 Li et al.
2015/0007833 A1* 1/2015 Orvis ................ A24F 13/14
131/328

FOREIGN PATENT DOCUMENTS

CN  101242436 A  8/2008
CN  203105624 U  8/2013
(Continued)

OTHER PUBLICATIONS

International Search Report corresponding to Application No. PCT/CN2014/075361; dated Apr. 15, 2014, with no English translation.

*Primary Examiner* — Alex Efta
(74) *Attorney, Agent, or Firm* — U.S. Fairsky LLP; Yue Xu

(57) ABSTRACT

An electronic cigarette capable of protecting the functional element on the surface of the main body of the electronic cigarette is provided. The main body of the electronic cigarette is provided with a functional element, a protection mechanism and a magnetic locating member; the protection mechanism is slidably connected to the main body of the electronic cigarette and is configured to cover the functional element; and the magnetic locating member is connected to the protection mechanism magnetically, and is configured to prevent the protection mechanism from randomly sliding on the main body of the electronic cigarette in a case that the functional element is exposed or covered by the protection mechanism. The present application avoids the exposure of the functional element, which prevents the functional element from being touched by mistake when the electronic cigarette is carried by the user, and allows the electronic cigarette to operate normally.

18 Claims, 12 Drawing Sheets

(51) Int. Cl.
*A24B 15/00* (2006.01)
*A24F 47/00* (2006.01)
*A61M 11/04* (2006.01)
*A61M 15/00* (2006.01)

(58) Field of Classification Search
CPC . A61M 15/0025; A24F 47/008; A24F 47/002; A24F 47/00
USPC .......................................... 131/329, 328, 360
See application file for complete search history.

(56) References Cited

FOREIGN PATENT DOCUMENTS

| | | |
|---|---|---|
| CN | 203194541 U | 9/2013 |
| CN | 203327954 U | 12/2013 |
| CN | 203388273 U | 1/2014 |

\* cited by examiner

ELECTRONIC CIGARETTE

CROSS REFERENCE

This application is a continuation under 35 U.S.C. § 120 of PCT/CN2014/075361, filed Apr. 15, 2014, which is incorporated herein reference.

TECHNICAL FIELD

The present application relates to the technical field of electronic cigarettes, and particularly relates to an electronic cigarette capable of protecting a functional element on a surface of a main body of the electronic cigarette.

BACKGROUND

With improved health awareness, more and more people realize that the harm of smoking, thus, an electronic cigarette, which is healthier than a real cigarette, becomes more and more popular.

In order to provide more functions for a user, manufacturers tend to arrange multiple functional elements on a main body of the electronic cigarette in designing the electronic cigarette. For example, a display may be provided for displaying a state of the electronic cigarette, and a push button may be provided on the main body of the electronic cigarette to control the operation of the electronic cigarette. Such elements bring a great enjoyment and pleasure to the user of the electronic cigarette.

Although a great enjoyment and pleasure has been provided for the user by such functional elements provided on the main body of the electronic cigarette, the push button or the display provided on the surface of the electronic cigarette also causes a lot of trouble for the user. Since these functional elements are exposed, these functional elements tend to be touched by mistake, or may be damaged by an impact when the electronic cigarette is carried by the user, which may cause the electronic cigarette unable to operate normally.

SUMMARY

An electronic cigarette is provided according to the present application, which is capable of protecting a functional element on a surface of a main body of the electronic cigarette.

A technical problem to be solved by the present application is that, since the functional element outside the main body of the electronic cigarette is exposed, these functional elements tend to be touched by mistake, or may be damaged by an impact when the electronic cigarette is carried by the user, which may cause the electronic cigarette unable to operate normally. To solve the technical problem, the following technical solutions are provided according to the present application.

An electronic cigarette includes:
a main body of the electronic cigarette;
wherein, a functional element, a protection mechanism and a magnetic locating member are provided on the main body of the electronic cigarette;
the protection mechanism is slidably connected to the main body of the electronic cigarette and is configured to cover the functional element; and
the magnetic locating member is connected to the protection mechanism magnetically, and is configured to prevent the protection mechanism from randomly sliding on the main body of the electronic cigarette in a case that the functional element is exposed or covered by the protection mechanism.

In the electronic cigarette of the present application, two ends of the protection mechanism are both provided with a retainer; and
the magnetic locating member is arranged between the retainers, and is configured to abut against the retainers to limit a sliding distance of the sleeve and prevent the protection mechanism from falling off the main body of the electronic cigarette.

In the electronic cigarette of the present application, the protection mechanism is a sleeve which is sleeved on the main body of the electronic cigarette;
each of the retainers is a retaining ring protruding out of an inner surface of the sleeve;
the magnetic locating member is a connecting ring; and
the connecting ring is arranged between the retainers and is configured to abut against the retaining rings to limit a sliding distance of the sleeve.

In the electronic cigarette of the present application, the connecting ring is provided with at least two slide grooves;
the sleeve is provided with slide rails which are configured to cooperate with the slide grooves and are slidable axially with respect to the main body of the electronic cigarette;
the retaining rings are arranged at two ends of the slide rails; and
the slide rails are arranged in an axial direction of the main body of the electronic cigarette.

In the electronic cigarette of the present application, each of the retaining rings is a magnet, and the connecting ring is made of ferrous materials; or, each of the retaining rings is made of ferrous materials, and the connecting ring is a magnet.

In the electronic cigarette of the present application, the protection mechanism is provided with an opening configured to allow a user to use the functional element;
the protection mechanism is provided with at least two circumferential grooves along a circumferential direction of the main body of the electronic cigarette;
the magnetic locating member is provided with circumferential protrusions configured to cooperate with the circumferential protrusions; and
the protection mechanism is slidable in the circumferential direction of the main body of the electronic cigarette through the cooperation between the circumferential grooves and the circumferential protrusions.

In the electronic cigarette of the present application, the sleeve is further provided with first retaining strips arranged at two sides of the opening in an axial direction of the main body of the electronic cigarette; and
the main body of the electronic cigarette is further provided with a second retaining strip for cooperating with the first retaining strips, and the second retaining strip is configured to abut against the first retaining strips to limit a sliding range of the protection mechanism.

In the electronic cigarette of the present application, each of the first retaining strips is a magnet, and the second retaining strip is made of ferrous materials; or, each of the first retaining strips is made of ferrous materials, and the second retaining strip is a magnet.

In the electronic cigarette of the present application, the functional element includes a push button and/or a display.

In the electronic cigarette of the present application, the main body of the electronic cigarette is further provided with a suction end, a liquid container for containing cigarette liquid, an atomizer assembly for atomizing the cigarette liquid, and a battery rod assembly for supplying power to the atomizer assembly; and the liquid container is arranged on the main body of the electronic cigarette at an end away from the suction end.

In the electronic cigarette of the present application, the atomizer assembly is arranged between the battery rod assembly and the liquid container, and the suction end is arranged at an outer side of an end of the battery rod assembly, in a middle of the battery rod assembly, or on the battery rod assembly at a position away from the atomizer assembly.

In the electronic cigarette of the present application, the liquid container is detachably connected to the atomizer assembly, and/or, the atomizer assembly is detachably connected to the battery rod assembly.

In the electronic cigarette of the present application, the atomizer assembly and the battery rod assembly are arranged coaxially.

In the electronic cigarette of the present application, the atomizer assembly includes:

a heating wire assembly for atomizing the cigarette liquid; and a liquid-guiding mechanism for delivering the cigarette liquid in the liquid container to the heating wire assembly to be atomized.

In the electronic cigarette of the present application, the atomizer assembly further includes:

an atomizer bracket;

a first thread bushing arranged at a top of the atomizer bracket and configured to be detachably connected to the battery rod assembly;

an atomizer electrode fixedly arranged inside the first thread bushing and electrically connected to the heating wire assembly;

an insulating ring arranged between the first thread bushing and the atomizer electrode; and an atomizing sleeve arranged on the atomizer bracket, and the liquid-guiding mechanism is arranged inside the atomizing sleeve.

In the electronic cigarette of the present application, a smoke channel for communicating the suction end with an air inlet is provided inside the battery rod assembly; and the air inlet is arranged on an abutting surface of the atomizer assembly and the liquid container; or, the air inlet is arranged on an outer wall of the atomizer assembly.

In the electronic cigarette of the present application, the battery rod assembly includes:

a battery casing;

a battery disposed inside the battery casing;

a battery bracket provided inside the battery casing to fix the battery;

a battery electrode arranged at an end of the battery bracket and electrically connected to the battery and the atomizer electrode; and a second thread bushing for cooperating with the first thread bushing to allow the battery rod assembly to be detachably connected to the atomizer assembly.

In the electronic cigarette of the present application, a sealing ring for sealing the liquid container is provided at a connection portion between the atomizer bracket and the liquid container.

In the electronic cigarette of the present application, an annular sealing plug with a through hole is provided to sealingly cooperate with an opening of the liquid container; and a pierceable membrane for sealing the liquid container is arranged inside the through hole of the annular sealing plug.

In the electronic cigarette of the present application, a non-metallic elastic member is connected to each of the retainers and is configured to elastically abut against a surface of the main body of the electronic cigarette, or each of the retainers is a non-metallic member.

Based on the above technical solutions, the embodiments of the present application have the following advantages.

The main body of the electronic cigarette in the present application is provided with a functional element, a protection mechanism and a magnetic locating member. The protection mechanism is slidably connected to the main body of the electronic cigarette and is configured to cover the functional element; and the magnetic locating member is connected to the protection mechanism magnetically, and is configured to prevent the protection mechanism from randomly sliding on the main body of the electronic cigarette in a case that the functional element is exposed or covered by the protection mechanism. Thus, when a user needs to use the functional element, he may remove the protection mechanism, and the protection mechanism can be reliably fixed by a magnetic force generated between the magnetic locating member and the protection mechanism, thereby preventing the protection mechanism from randomly sliding and avoiding affecting the user using the functional element; and when the user does not need to use the functional element, the protection mechanism is covered on the functional element to protect it, and the protection mechanism can be reliably fixed by the magnetic force. The present application avoids the exposure of the functional element, which prevents the functional element from being touched by mistake when the electronic cigarette is carried by the user, and allows the electronic cigarette to operate normally. In addition, the protection mechanism is fixed by the magnetic locating member, thus the protection mechanism may slide smoothly, which is convenient for the user, and improves the user experience. Further, by using the magnetic force, a fatigue problem raised by using an elastic element may be avoided, thereby improving the service life.

BRIEF DESCRIPTION OF THE DRAWINGS

In order to more clearly illustrate the embodiments of the present application or the technical solution in the conventional technology, drawings referred to describe the embodiments or the conventional technology will be briefly described hereinafter. Apparently, the drawings in the following description are only a few of embodiments of the present application, and for the person skilled in the art, other drawings may be obtained based on these drawings without any creative efforts.

DETAILED DESCRIPTION

The technical solutions in the embodiments of the present application will be described clearly and completely hereinafter in conjunction with the drawings in the embodiments of the present application. Apparently, the described embodiments are only a part of the embodiments of the present application, rather than all embodiments. All of other embodiments, made by the person skilled in the art without any creative efforts based on the embodiments in the present application, fall into the scope of the present application.

Figure 1:
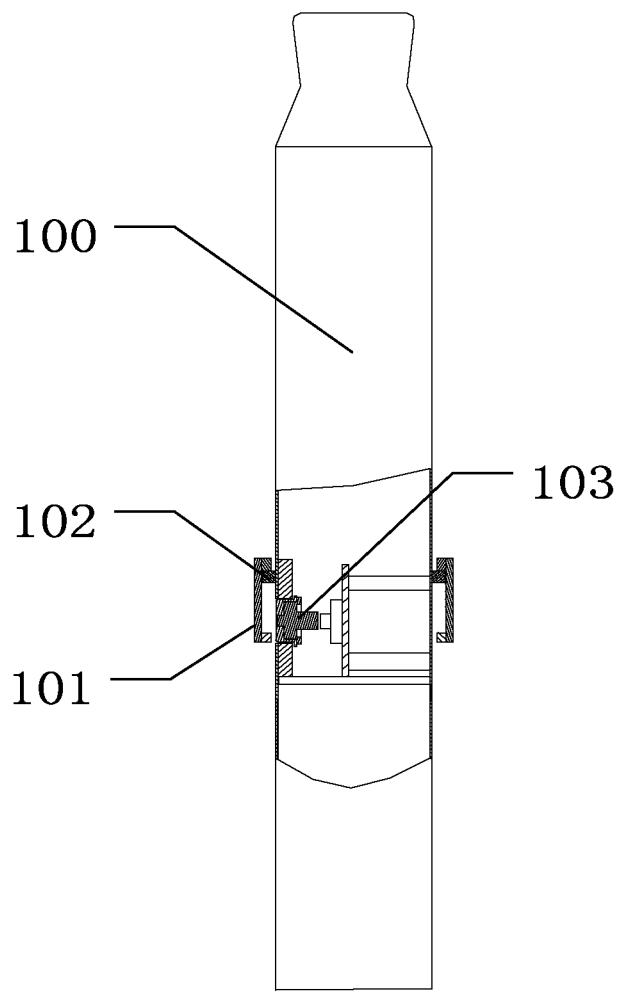
FIG. 1 is a schematic view showing an overall structure of an electronic cigarette according to the present application.

An electronic cigarette is provided by the present application, which is capable of protecting a functional element on a surface of a main body of the electronic cigarette. Reference is made to FIG. 1. A main body 100 of the electronic cigarette is provided with a functional element 103, a protection mechanism 101, and a magnetic locating member 102.

The protection mechanism 101 is slidably connected to the main body 100 of the electronic cigarette, and is configured to cover the functional element 103. The magnetic locating member 102 is connected to the protection mechanism 101 magnetically, and is configured to prevent the protection mechanism 101 from moving randomly on the main body 100 of the electronic cigarette when the functional element 103 is exposed or covered by the protection mechanism 101. In this embodiment, the magnetic locating member 102 is fixedly connected to an exterior of the main body 100 of the electronic cigarette. Certainly, the magnetic locating member 102 may also be movable arranged or arranged inside the main body 100 of the electronic cigarette, which is not limited here.

The protection mechanism 101 is slidably connected to the main body 100 of the electronic cigarette, thus when a user needs to use the functional element 103, he may remove the protection mechanism 101, and the protection mechanism 101 can be reliably fixed by a magnetic force generated between the magnetic locating member 102 and the protection mechanism 101, thereby preventing the protection mechanism 101 from sliding randomly and avoiding affecting the user using the electronic cigarette. When the user does not need to use the functional element 103, the protection mechanism 101 is covered on the functional element 103 to protect it, and the protection mechanism 101 can be reliably fixed by the magnetic force. The present application avoids the exposure of the functional element 103, which prevents the functional element 103 from being touched by mistake, and allows the electronic cigarette to operate normally. In addition, the protection mechanism 101 is fixed by the magnetic locating member 102, thus the protection mechanism 101 may be slide smoothly, which is convenient for the user and improves the user experience. Further, by using the magnetic force, a fatigue problem tending to happen when an elastic element is used can be avoided, thereby ensuring a longer service life.

In the embodiment of the present application, the protection mechanism 101 may be made of a magnetic material which can generate an attraction to a magnet, such as Fe, Co, Ni or an alloy thereof; alternatively, the protection mechanism 101 may be provided with a magnetic material, such as Fe, Co, Ni or an alloy thereof. The magnetic locating member 102 is fixedly connected to the main body 100 of the electronic cigarette, and the magnetic locating member 102 generates a magnetic attraction force to attract the protection mechanism 101, thus the protection mechanism 101 is connected to the magnetic locating member 102 by the magnetic attraction force, and when being pushed by a user, the protection mechanism 101 is slidable on the exterior of the main body 100 of the electronic cigarette.

The protection mechanism 101 shown in FIG. 1 is wholly sleeved on the main body 100 of the electronic cigarette to cover the functional element 103.

Figure 2:
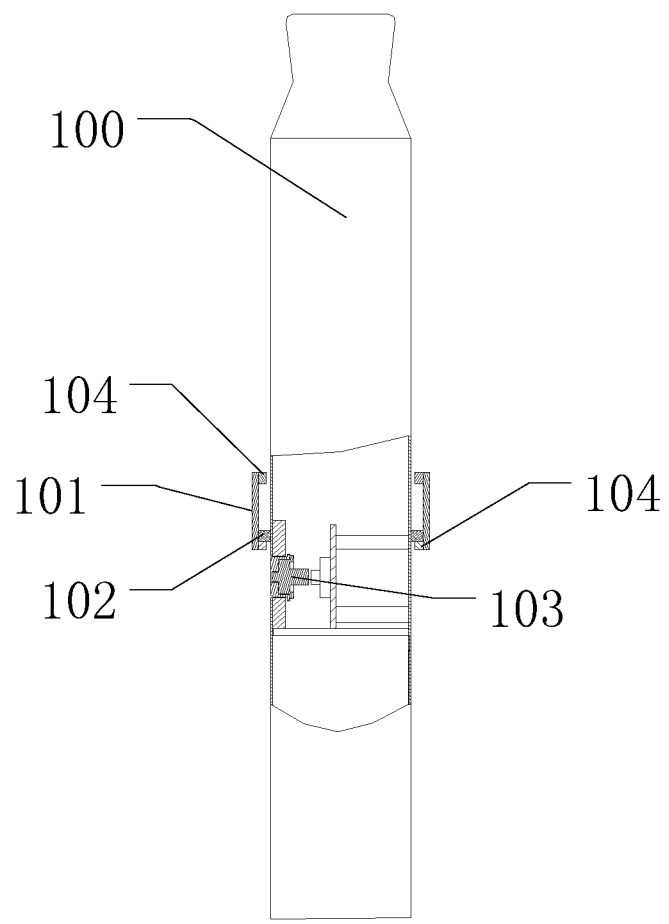
FIG. 2 is a schematic view showing the overall structure of the electronic cigarette according to the present application with a protection mechanism being opened.

As shown in FIG. 2, when being pushed by a user, the protection mechanism 101 exposes the functional element 103, and then the user may use the functional element 103 normally.

A length of the protection mechanism 101 in a longitudinal direction of the main body 100 of the electronic cigarette may be equal to or greater than a length of the functional element in the longitudinal direction of the main body 100 of the electronic cigarette, but cannot exceed one third of a length of the main body 100 of the electronic cigarette, and the specific length is not limited here.

The magnetic locating member 102 may be arranged as a ring surrounding a circumference of the main body 100 of the electronic cigarette. A number of the annular magnetic locating member 102 may be two, three, or four, and the specific number is not limited here.

The annular magnetic locating member 102 may be a broken ring or an integral ring.

The magnetic locating member 102 may be arranged along an axial direction of the main body 100 of the electronic cigarette, and have a length equal to or less than the length of the protection mechanism 101 along the main body 100 of the electronic cigarette, but cannot less than two-thirds of the length of the protection mechanism 101. The specific shape of the magnetic locating member 102 is not limited here.

In the present application, the protection mechanism 101 may be pushed by the user to slide on the exterior of the main body 100 of the electronic cigarette, and in some cases, the protection mechanism 101 may fall off the main body 100 of the electronic cigarette, thus losing the function of protecting the functional element 103. As shown in FIG. 2, two ends of the protection mechanism 101 are both provided with a retainer 104. The magnetic locating member 102 is arranged between the retainers 104, and is configured to abut against the retainer 104, to limit a sliding distance of the protection mechanism 101, and prevent the protection mechanism 101 from falling off the main body 100 of the electronic cigarette.

In the present application, the protection mechanism 101 is in an interference fit with the magnetic locating member 102, thus the protection mechanism 101 and the magnetic locating member 102 are slidable with respect to each other, and have a smooth sliding surface therebetween. In this case, the protection mechanism 101 can have a better protection function, and when the electronic cigarette is used by the user, a sliding direction of the protection mechanism 101 is controllable.

In the present application, the functional element 103 includes a push button and/or a display, and further includes a module or component to be protected which has to be arranged on the exterior of the main body 100 of the electronic cigarette to add the functions of the electronic cigarette. The specific member or component is not limited here.

In order to describe the present application more sufficiently, implementations are described by the following embodiments.

Figure 3:
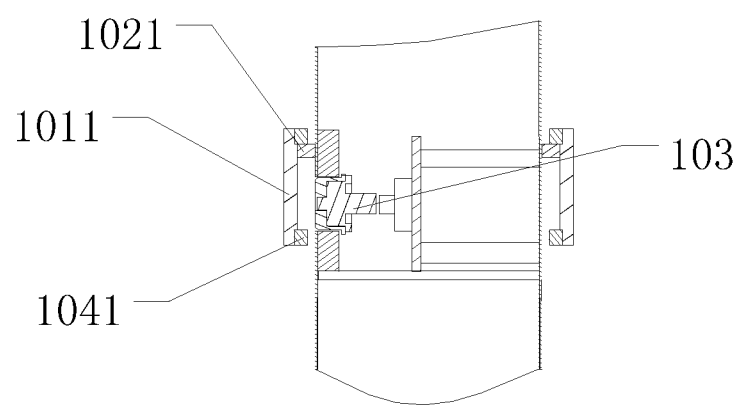
FIG. 3 is a schematic view showing another embodiment of the electronic cigarette according to the present application.

In a first embodiment shown in FIG. 3, the protection mechanism is a sleeve 1011 sleeved on the main body of the electronic cigarette, and this structure is easy to assemble and has a reliable connection. Certainly, the protection mechanism may also have other structures, such as a tile-shaped structure, which is not limited here. The retainers 104 are embodied as retaining rings 1041 protruding out of an inner surface of the sleeve, and the retaining rings 1041 are mounted in the annular grooves 1053 on an inner wall of the sleeve 1011. The magnetic locating member 102 is embodied as a connecting ring 1021 sleeved on the main body 100 of the electronic cigarette. The connecting ring 1021 is arranged between the retaining rings 1041, and can be used to abut against the retaining rings 1041, to limit the sliding distance of the sleeve 1011. In order to prevent the retainers 104 from scratching the surface of the main body of the electronic cigarette, the retainers are each connected to a non-metallic elastic member elastically abutting against the surface of the main body of the electronic cigarette; alternatively, the retainers are embodied as non-metallic elastic members. The non-metallic elastic member may be made of silica gel or rubber, which is not limited here.

Figure 4:
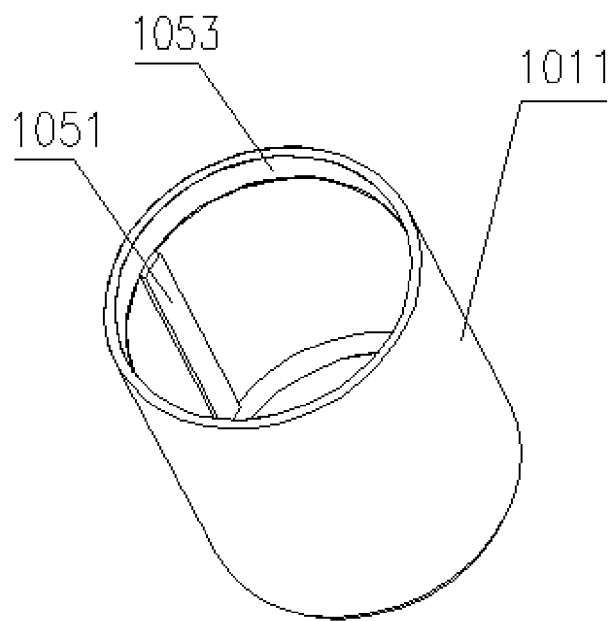
FIG. 4 is a schematic view showing the structure of a sleeve of the electronic cigarette according to the present application.
Figure 5:
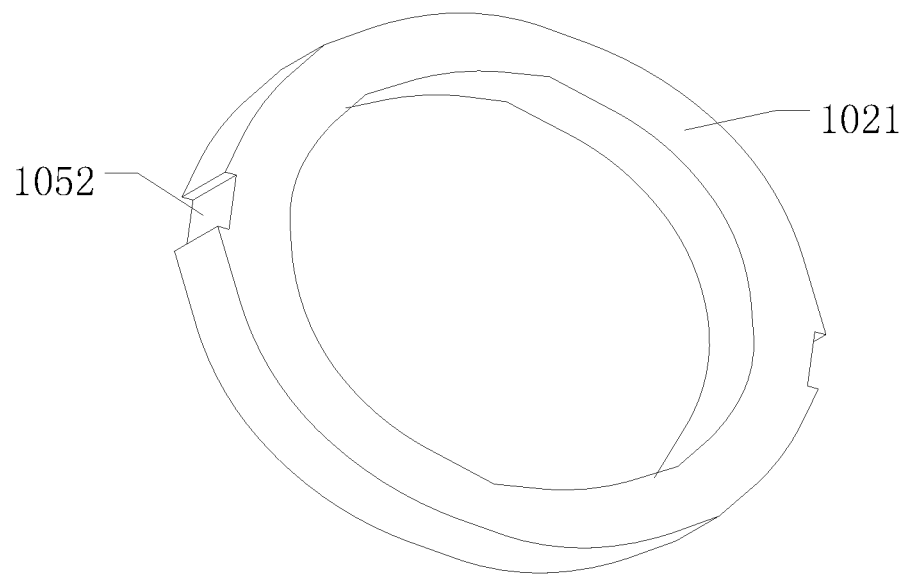
FIG. 5 is a schematic view showing the structure of a connecting ring of the electronic cigarette according to the present application.

In this embodiment, referring to FIG. 4 and FIG. 5, the connecting ring 1021 is provided with at least two slide grooves 1052; and the sleeve 1011 is provided with slide rails 1051 for cooperating with the slide grooves 1052, to allow the sleeve to slide with respect to the main body 100 of the electronic cigarette in the axial direction. The retaining rings 1041 are arranged at two ends of the slide rails 1051. The slide rails 1051 are arranged in the axial direction of the main body 100 of the electronic cigarette.

The sleeve 1011 is slidable with respect to the main body 100 of the electronic cigarette. When a user needs to use the functional element 103, he may slide open the sleeve 1011, and if the user does not need to use the functional element 103, he can use the sleeve 1011 to cover the functional element 103 to protect the functional element 103. In this case, the exposure of the functional element 103 is avoided, thereby preventing the functional element from being touched by mistake when the user carries the electronic cigarette, and ensuring the normal operation of the electronic cigarette.

In this embodiment, the length of the sleeve 1011 in the axial direction of the main body of the electronic cigarette may be configured to be same as or slightly greater than the length of the functional element 103. The length of the sleeve 1011 is not limited here, as long as the sleeve can cover all the functional elements.

In this embodiment, the connecting ring 1021 is fixed on the main body 100 of the electronic cigarette, and is arranged inside the sleeve 1011 between the retaining rings 1041. In order to prevent the sleeve 1011 from falling off the main body 100 of the electronic cigarette, a circumferential width of the connecting ring 1021, i.e. the thickness of the connecting ring 1021, is configured to allow the connecting ring 1021 to just in contact with the inner surface of the sleeve or to provide a distance between the connecting ring 1021 and the inner surface of the sleeve. By configuring the circumferential width of the connecting ring 1021 in this manner, the circumferential width of the retaining ring 1041, i.e., the thickness of the retaining ring 1041, can allow a side of the connecting ring 1021 to be in contact with a side of the respective retaining ring 1041 when the sleeve 1011 slides to one end. Further, whether the sleeve 1011 slides in the axial direction or the circumferential direction, the side of the connecting ring 1021 can always in contact with the side of the respective retaining ring 1041, to prevent the sleeve 1011 from sliding further. Thus, the sleeve 1011 cannot be prevented from falling off the main body 100 of the electronic cigarette.

In this embodiment, the sleeve 1011 is slidable on the main body 100 of the electronic cigarette due to the cooperation between the slide rails 1051 and the slide grooves 1052, and a sliding distance of the sleeve 1011 may allow the sleeve 1011 to cover the functional element. When the sleeve is slid open, the user may use the functional element 103 normally without being affected by the sleeve. In order to realize a better cooperation between the slide rails 1051 and the slide grooves 1052, the slide rails 1051 and the slide grooves 1052 may be both configured to have an isosceles trapezoid cross section, in this way, the slide rails 1051 and the slide grooves 1052 may form snap fits, and realize a reliable connection.

In this embodiment, the number of the slide grooves 1052 of the connecting ring 1021 may be configured as three, four or more. By providing more slide grooves 1052, the stability of the cooperation between the slide rails 1051 and the slide grooves 1052 is improved, that is, the stability of the connection between the sleeve 1011 and the main body of the electronic cigarette is improved. In this embodiment, it is preferably to arrange three slide grooves 1052. Three slide grooves 1052 can form a stable cooperation, thus the sleeve 1011 would not swing on the main body 100 of the electronic cigarette. If too many slide grooves 1052 are provided, the manufacturing process will be complicated. Three slide grooves 1052 are configured to cooperate with three slide rails. Herein, the specific number is not limited.

In this embodiment, in order to allow the user to use the sleeve 1011 more convenient, the retaining rings 1041 are embodied as magnets, and the connecting ring 1021 is made of ferrous material. By employing magnets as the retaining rings 1041 and the connecting ring 1021 made of ferrous material, the user can operate the functional element when the sleeve 1011 is slid to one side to expose the functional element 103, and because the magnet of the retaining ring 1041 and the ferrous material of the connecting ring 1021 attract each other, the sleeve is tightly sucked at this side and cannot slide freely, thereby not affecting the user using the functional element. Similarly, when the functional element is covered by the sleeve 1011, the magnet of the retaining ring 1041 and the ferrous material of the connecting ring 1021 attract each other, thus the sleeve 1011 can stably cover the functional element 1031 and will not slide open freely.

Certainly, in another embodiment, the retaining rings are made of ferrous material, and the connecting ring is embodied as a magnet. The specific operation manner and effect of this embodiment are same as the above embodiment, thus will not be described here.

In this embodiment, the sleeve 1011 is made of plastic cement. Since the retaining rings 1041 and the connecting ring 1021 employ a magnet and/or ferrous material, and the sleeve employs a nonferrous material, the sleeve will not be attracted by the magnet, thereby avoiding affecting the user using the electronic cigarette. Since the plastic cement is wear resistant, the sleeve arranged outside the main body 100 of the electronic cigarette can provide a good hand feeling for the user. Thus, the sleeve may be preferably made of plastic cement. Other materials can also be used, which is not limited here.

In the present application, another embodiment is provided. The difference between this embodiment and the above embodiment lies in the sliding direction of the protection mechanism 101. In the above embodiment, the protection mechanism 101 slides in the axial direction of the main body 100 of the electronic cigarette. In this embodiment, the protection mechanism 101 slides in the circumferential direction of the main body 100 of the electronic cigarette. However, the protection mechanism 101 in the two embodiments has the same function.

The protection mechanism 101 is provided with an opening for allowing the user to operate the functional element 103. The protection mechanism is provided with at least two circumferential grooves along the circumferential direction of the main body 100 of the electronic cigarette. The magnetic locating member 102 is provided with circumferential protrusions for cooperating with the circumferential grooves. The protection mechanism 101 is slidable in the circumferential direction of the main body 100 of the electronic cigarette by the cooperation between the circumferential grooves and the circumferential protrusions.

In this embodiment, the magnetic locating member is provided with the protrusions, the protection mechanism 101 is provided with the grooves for cooperating with the protrusions. The protrusions and the grooves are both arranged in the circumferential direction of the main body of the electronic cigarette. The number of the protrusions may be two, three or four, and the specific number is not limited here. The number of the grooves is corresponding to the number of the protrusions.

In this embodiment, the protection mechanism 101 is provided with an opening having an area equal to or larger than an area of the functional element 103. When the protection mechanism 101 is rotated circumferentially to allow the opening to coincide with the functional element 103, the user may operate the functional element 103. When the user does not need to use the functional element 103, the protection mechanism 101 is rotated circumferentially to move the opening away from the functional element 103, thereby protecting the functional element 103.

In this embodiment, the protection mechanism 101 is also provided with a first retaining strip arranged at two sides of the opening in the axial direction of the main body of the electronic cigarette. The main body of the electronic cigarette is also provided with a second retaining strip for cooperating with the first retaining strips to limit the range of the sliding of the protection mechanism.

The first retaining strips are arranged at two sides of the opening, and the second retaining strip is arranged between the two first retaining strips. The two first retaining strips may be in contact with the second retaining strip, to stop the circumferential sliding of the protection mechanism, thereby controlling a circumferential sliding distance of the protection mechanism and controlling the functional element to slide between the two first retaining strips. A distance between the two first retaining strips is an area of the functional element, and mal also be larger than the area of the functional element. This manner may allow the user to operate the electronic cigarette conveniently, and the user does not need to rotate the opening of the protection mechanism to locate the functional element.

In this embodiment, the first retaining strips are embodied as magnets, and the second retaining strip is made of ferrous material. In the manner using the attraction between the magnet and the ferrous material, the user can operate the functional element when the user aligns the opening with the functional element, and due to the attraction between the magnet of the first retaining strip and the ferrous material of the second retaining strip, the sleeve is tightly sucked at one side and cannot slide freely, thereby not affecting the user using the functional element. Similarly, when the functional element is covered by the protection mechanism, the protection mechanism can stably cover the functional element and cannot slide freely due to the attraction between the magnet of the first retaining strip and the ferrous material of the second retaining strip.

Certainly, in another embodiment of the present application, the first retaining strips may be made of ferrous material, and the second retaining strip may be embodied as a magnet. The specific operation manner and effect of this embodiment are same as the above embodiment, thus will not be described here.

Figure 6:
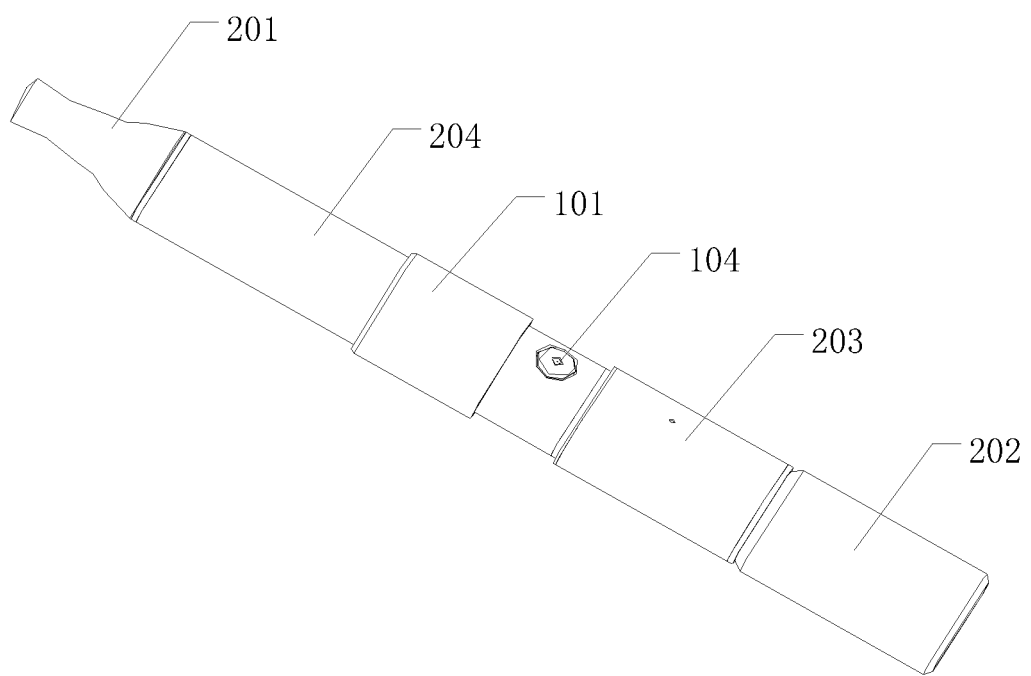
FIG. 6 is a schematic view showing the overall structure of another preferred embodiment of the electronic cigarette according to the present application.

In the present application, referring to FIG. 6, which is a schematic view showing the overall structure of the electronic cigarette according to the present application, the main body of the electronic cigarette further includes a suction end 201. A user may smoke via the suction end 201.

The main body of the electronic cigarette further includes a liquid container 202 for containing cigarette liquid, and the cigarette liquid to be atomized is stored in the liquid container 202.

The main body of the electronic cigarette further includes an atomizer assembly 203 for atomizing the cigarette liquid, and the cigarette liquid in the liquid container 202 can be atomized by the atomizer assembly 203.

A smoke channel (not shown) for circulating the atomized cigarette liquid is formed in the main body of the electronic cigarette, to allow the user to smoke, via the suction end 201, the cigarette liquid passing through the smoke channel.

The main body of the electronic cigarette further includes a battery rod assembly 204 for supplying power to the atomizer assembly 203.

As shown in FIG. 6, the liquid container 202 is arranged at an end of the main body of the electronic cigarette that is away from the suction end 201. Such arrangement has the following advantage, the smoke channel in the main body of the electronic cigarette does not pass through the liquid container 202 since the liquid container 202 is arranged away from the suction end 201, thus the cigarette liquid in the liquid container 202, which is not atomized, will not leak into the smoke channel, thereby ensuring that the user will not smoke the cigarette liquid which is not atomized, avoiding a leakage of the cigarette liquid effectively. Further, by arranging the smoke channel to not pass through the liquid container 202 may also prevent the smoke from being condensed in the smoke channel, thereby effectively avoiding condensed smoke blocking the smoke channel.

The specific structure of the electronic cigarette of the present application is further described in detail in conjunction with FIG. 6. The atomizer assembly 203 is arranged between the battery rod assembly 204 and the liquid container 202. The suction end 201 is arranged at an outer side of one end of the battery rod assembly 204, or at a middle of the battery rod assembly 204, or on the battery rod assembly 204 at a position away from the atomizer assembly 203.

The suction end 201 arranged at the outer side of the end of the battery rod assembly 204 may be configured to be coaxial with the battery rod assembly 204. Such arrangement may allow the appearance of the electronic cigarette to directly imitate a real cigarette, provide a straight smoke channel, and effectively reduce liquid accumulation.

The suction end 201 may also be arranged at the middle of the battery rod assembly 204, or arranged on the battery rod assembly 204 at a position away from the atomizer assembly 203.

In the present application, the specific position of the suction end 201 is not limited.

In this embodiment, the atomizer assembly 203 may be configured to be coaxial with the battery rod assembly 204, so as to make the entire structure of the electronic cigarette imitate the real cigarette, to conform to the using habit of the user and reduce the liquid accumulation.

Certainly, the specific arrangement is not limited in this embodiment. For example, the battery rod assembly 204, the atomizer assembly 203, and the liquid container 202 which are connected sequentially can be arranged staggeredly, to make the electronic cigarette have an irregular shape, and the irregular shape may be any shape.

The atomizer assembly 203 and the battery rod assembly 204 may also be arranged in a non-coaxial manner. The liquid container 202 and the atomizer assembly 203 may be configured in parallel, and both of the liquid container 202 and the atomizer assembly 203 are respectively connected to the battery rod assembly 204, thereby allowing the electronic cigarette to have a T-shaped overall structure.

In this embodiment, the overall shape of the electronic cigarette is not limited, as long as the liquid container 202 is arranged at a position away from the suction end 201.

In this embodiment, the atomizer assembly 203 is arranged between the battery rod assembly 204 and the liquid container 202, that is, the atomizer assembly 203 is away from the suction end 201. When a user is smoking an electronic cigarette according to this embodiment, the user will not be scalded by the heat generated by the atomizer assembly 203 atomizing the cigarette liquid, since the atomizer assembly 203 is away from the mouth of the user, thereby effectively enhancing the use safety of the electronic cigarette. In addition, the user usually holds the battery rod assembly 204 when smoking the electronic cigarette, thereby avoiding the problem in the conventional technology that the user holds the hot atomizer assembly 203 when smoking. In this case, when the user is smoking the electronic cigarette according to this embodiment, the hand of the user will not be scalded, and the electronic cigarette according to this embodiment also effectively imitates the temperature of a real cigarette, thereby improving the user experience in smoking.

Preferably, the liquid container 202 may be detachably connected to the atomizer assembly 203 and/or the atomizer assembly 203 may be detachably connected to the battery rod assembly 204.

Specifically, the connection manner between the liquid container 202 and the atomizer assembly 203 and/or the atomizer assembly 203 and the battery rod assembly 204 may be a threaded connection or a snap fit, and etc. The specific connection manner is not limited in this embodiment, as long as the liquid container 202 and the atomizer assembly 203 are detachably connected and/or the liquid container 202 and the battery rod assembly 204 are detachably connected.

The above detachable connection manner may allow the user to replace the atomizer assembly 203 or detach the liquid container 202 at any time conveniently, thereby facilitating the user filling the cigarette liquid into the liquid container 202 or replacing the liquid container 202. Certainly, the connection manner between the liquid container 202 and the atomizer assembly 203 and/or between the atomizer assembly 203 and the battery rod assembly 204 may also be a non-detachable manner, which is not limited here.

Figure 7:
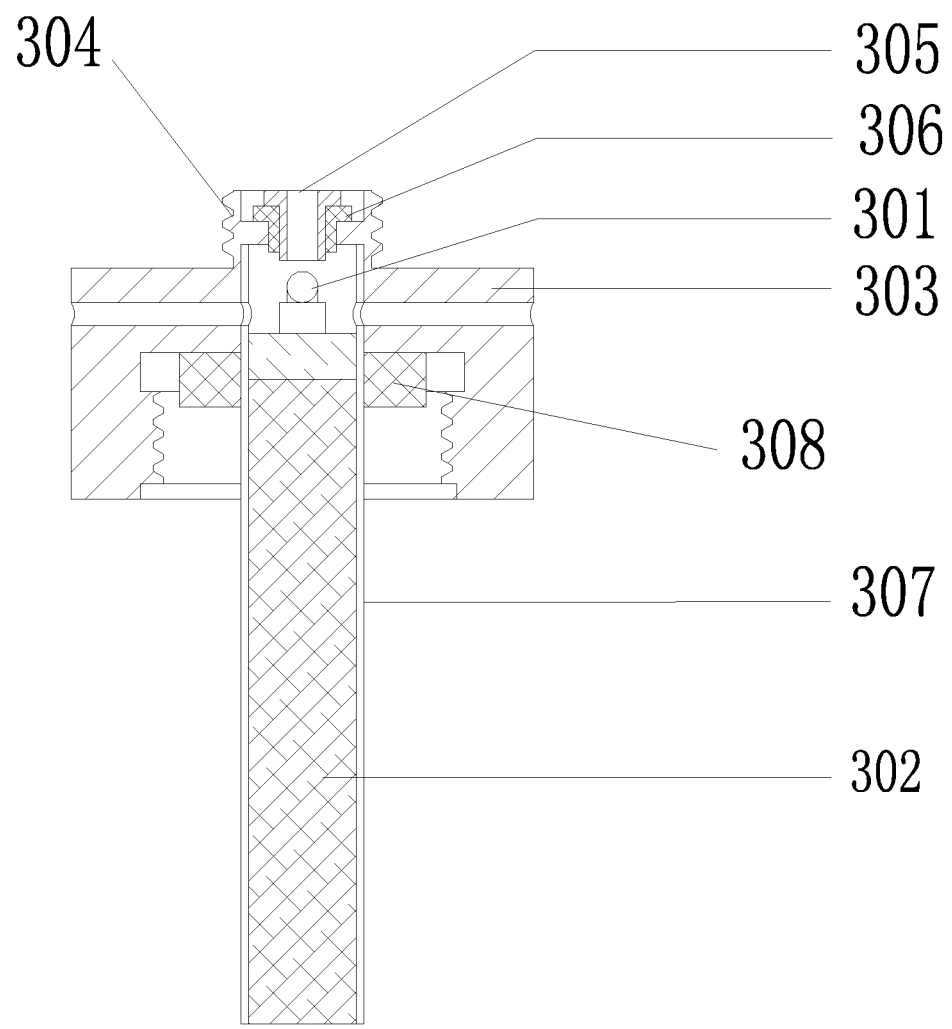
FIG. 7 is a sectional view showing the structure of a preferred embodiment of an atomizer assembly of the electronic cigarette according to the present application.

The specific structure of the atomizer assembly of the electronic cigarette is described in detail in conjunction with the embodiment shown in FIG. 7.

As shown in FIG. 7, the atomizer assembly 203 includes an atomizer bracket 303.

A top of the atomizer bracket 303 is provided with a first thread bushing 304 configured to be detachably connected to the battery rod assembly 204.

The connection between the atomizer assembly 203 and the battery rod assembly 204 is illustrated as a thread connection in this embodiment as an example, that is, in the case that the atomizer assembly 203 and the battery rod assembly 204 are connected by thread connection, the first thread bushing 304 is provided on the top of the atomizer bracket 303. In the case that other detachable connection structures are employed, other connection structures, such as an elastic snap piece in snap fit, may be provided on the top of the atomizer bracket 303. In this embodiment, the thread bushing is only illustrated as an example, and the connection structure is not limited to the thread bushing.

The atomizer assembly 203 further includes an atomizer electrode 305 fixedly arranged inside the first thread bushing 304.

An insulating ring 306 is arranged between the first thread bushing 304 and the atomizer electrode 305.

A heating wire assembly 301 is electrically connected to the atomizer electrode 305, and is used to atomize the cigarette liquid.

A liquid-guiding mechanism 302 is provided for delivering the cigarette liquid in the liquid container 202 to the heating wire assembly 301 to be atomized. Specifically, the liquid-guiding mechanism 302 may use liquid storage cotton, liquid-guiding fiber, and etc., which is not limited here.

An atomizing sleeve 307 is arranged on the atomizer bracket 303, and the liquid-guiding mechanism 302 is arranged inside the atomizing sleeve 307.

The atomizing sleeve 307 is inserted into the liquid container 202, and a circumferential wall of the atomizing sleeve 307 is provided with at least one liquid hole, and the cigarette liquid inside the liquid container 202 can be smoothly delivered to the liquid-guiding mechanism 302 via the liquid hole.

Figure 8:
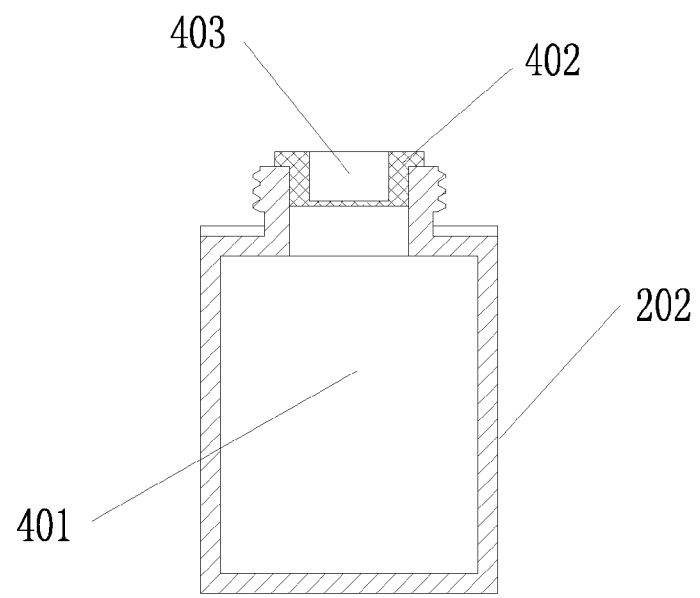
FIG. 8 is a sectional view showing the structure of a preferred embodiment of a liquid container of the electronic cigarette according to the present application.

The specific structure of the liquid container of the present application is described in detail in conjunction with the embodiment as shown in FIG. 8.

As shown in FIG. 8, the liquid container 202 has a seal cavity 401 inside, and the cigarette liquid is stored in the seal cavity 401 sealingly.

The liquid container 202 may be configured as a transparent container to allow a user to aware of the remaining amount of the cigarette liquid in the liquid container 202. That is, the user can know the remaining amount of the cigarette liquid in the electronic cigarette via the transparent liquid container 202 at any time, thus, the user can replace the liquid container 202 in time.

Preferably, the liquid container 202 is a glass bottle. Since glass is a stable material, it can avoid chemical reaction, thus the smoking taste will not be affected.

More preferably, a scale is provided on the circumferential wall of the liquid container 202, thus the user may be able to estimate that how long the remaining cigarette liquid can be used, which further facilitates using the electronic cigarette.

Preferably, a protective casing (not shown) may be sleeved on the liquid container 202, to protect the glass liquid container 202 from being damaged when falling off.

More preferably, the protective casing is provided with a cigarette liquid viewing window to allow the user to observe the cigarette liquid.

In order to imitate a real cigarette, the length of the electronic cigarette is generally equal to the length of the real cigarette, and in order to reduce the charging frequency and increase the service life of the battery rod assembly 204, the length of the battery rod assembly 204 is at least greater than a half of the length of the entire electronic cigarette. When a user smokes an electronic cigarette according to this embodiment, he would naturally hold the electronic cigarette at a middle-top part close to the suction end 201. Since the liquid container 202 in this embodiment is arranged at an end away from the suction end 201, the liquid container 202 will not suffer a holding force from the user, thus the cigarette liquid may be output from the liquid container 202 to the atomizer assembly 203 stably, which effectively ensures a stable smoke output and improving the user experience, thereby avoiding the situation in the convention technology that, the smoke output is uneven since the supply of the cigarette liquid varies with the force applied on the end of the liquid container by the user.

In order to ensure an excellent sealing of the liquid container 202 and effectively avoid the leakage of the cigarette liquid, two arrangements can be employed in this embodiment.

The first arrangement is shown in FIG. 3, in order to ensure an excellent sealing of the liquid container 202 connected to the atomizer assembly 203, to further avoid leakage of the cigarette liquid in the liquid container 202, a sealing ring 308 for sealing the liquid container 202 is provided on the atomizer bracket 303 at a position where the atomizer bracket 303 and the liquid container 202 are connected.

The sealing ring 308 provided on the atomizer bracket 303 may effectively ensure the sealing of the liquid container 202.

In the second arrangement shown in FIG. 8, an annular sealing plug 402 with a through hole is provided for sealingly cooperating with the opening of the liquid container 202.

A pierceable membrane 403 for sealing the liquid container 202 is provided inside the through hole of the annular sealing plug 402.

When the atomizing sleeve 307 is inserted into the seal cavity 401 of the liquid container 202, the atomizing sleeve 307 passes through the pierceable membrane 403. Due to the pierceable membrane 403, the liquid container 202 with the atomizing sleeve 307 being inserted therein still has an excellent sealing, thereby effectively avoiding leakage of the cigarette liquid.

Since the liquid container 202 in this embodiment is provided with the annular sealing plug 402 with the pierceable membrane 403, the liquid container 202 has an excellent sealing, thereby effectively avoiding leakage of the cigarette liquid, prolonging the service time of the electronic cigarette, and ensuring the service life of the electronic cigarette.

Figure 9:
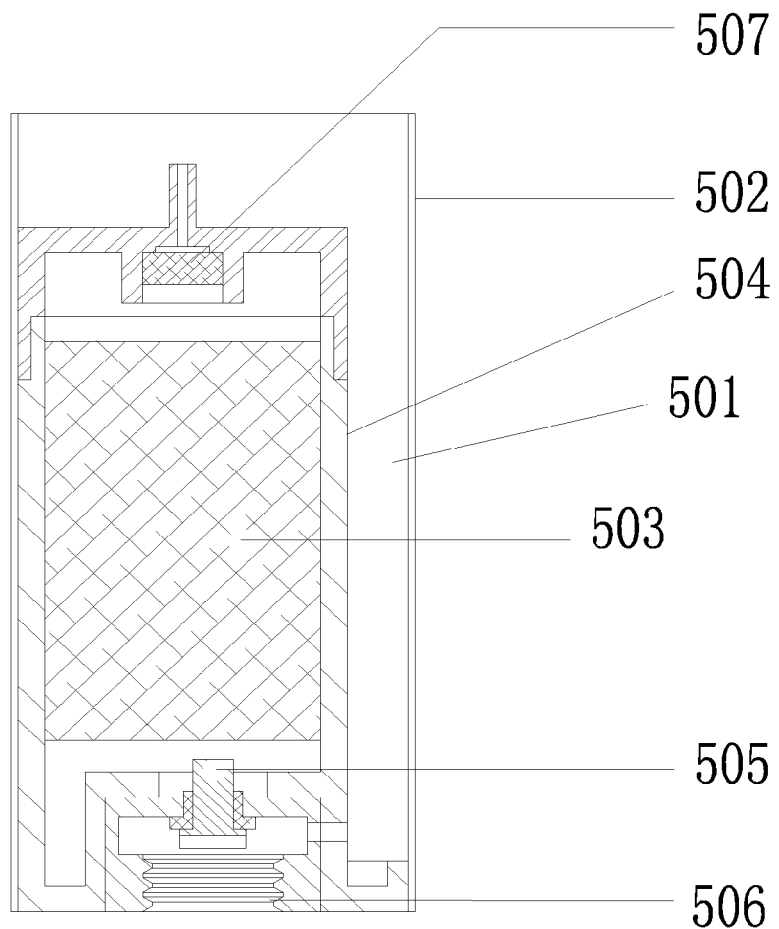
FIG. 9 is a sectional view showing the structure of a preferred embodiment of a battery rod assembly of the electronic cigarette according to the present application.

The specific structure of the battery rod assembly of the electronic cigarette of the present application is described in detail in conjunction with the embodiment shown in FIG. 9.

As shown in FIG. 9, the battery rod assembly includes a battery casing 502.

The suction end 201 in FIG. 2 may be integrally formed by an extension of the end of the battery casing 502, or, a suction nozzle functioning as the suction end 201 may be detachably connected to the battery casing 502, and the specific connecting manner is not limited here.

The detachably connected suction nozzle functioning as the suction end 201 in this embodiment may be replaced or washed by the user at any time, thereby preventing the user from sucking the cigarette liquid in the suction nozzle, and facilitating cleaning the cigarette liquid in the battery rod assembly.

The battery rod assembly further includes a battery 503 arranged in the battery casing 502;

a battery bracket 504 arranged in the battery casing 502 to fix the battery 503;

a battery electrode 505 arranged at an end of the battery bracket 504 and connected to the battery 503 and the atomizer electrode 305 (as shown in FIG. 7); and a second thread bushing 506 configured to cooperate with the first thread bushing 304 (as shown in FIG. 7) to detachably connect the battery rod assembly 204 to the atomizer assembly 203.

Certainly, the connection between the battery rod assembly 204 and the atomizer assembly 203 is illustrated as the thread connection in this embodiment as an example. It is to be noted that, the battery rod assembly 204 and the atomizer assembly 203 may also be detachably connected by other manners, which is not limited here.

Reference is further made to FIG. 9. A smoke channel 501 for communicating the suction end 201 with the air inlet is provided inside the battery rod assembly 204.

Preferably, the smoke channel 501 is sealingly provided in the battery rod assembly 204, that is, the smoke channel 501 is isolated from other electronic elements in the battery rod assembly 204.

Two arrangements for the air inlet in communication with the smoke channel 501 may be provided. It is to be noted that, the following arrangements for the air inlet are only illustrated as an example, which is not limited herein, and other arrangements are also used as long as the air inlet of the main body of the electronic cigarette can be communicated with the suction end 201 through the smoke channel 501.

In the first arrangement, the air inlet may be provided on an abutting surface of the atomizer assembly 203 and the liquid container 202. Specifically, a protrusion or a protruding rib is provided at the abutting surface of the atomizer assembly 203 and the liquid container 202, thus an air inlet allowing air to flow in is formed between the atomizer assembly 203 and the liquid container 202 which are threadedly connected, and air can flow into the smoke channel 501 through the air inlet.

It is to be noted that, the arrangement of the air inlet is not limited, as long as an air inlet allowing air to flow in can be formed between the atomizer assembly 203 and the liquid container 202.

Figure 10:
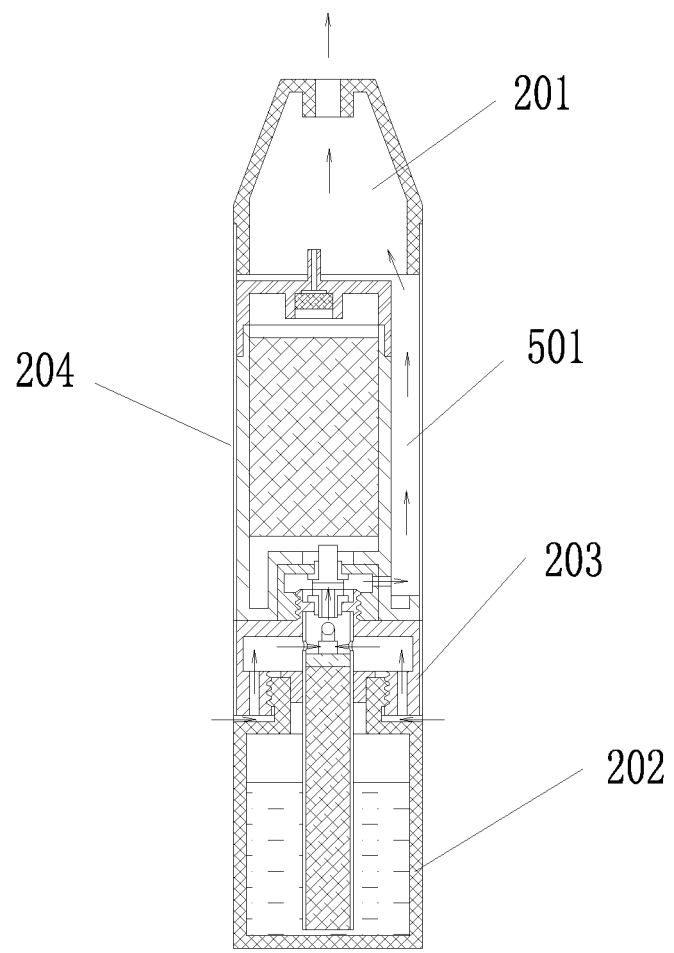
FIG. 10 is a sectional view showing the structure of another preferred embodiment of the electronic cigarette according to the present application.

The suction end 201 may be communicated with the air inlet through the smoke channel 501, which can be referred to FIG. 10. FIG. 10 is a sectional schematic view of the electronic cigarette, in which the air inlet is arranged on the abutting surface of the atomizer assembly 203 and the liquid container 202.

As shown in FIG. 10, the air inlet arranged on the abutting surface of the atomizer assembly 203 and the liquid container 202 is communicated with the suction end 201 via the smoke channel 501.

In this embodiment, the direction of the air flow in the electronic cigarette is indicated by arrows, and as shown in FIG. 10, the air flow does not pass through the liquid container 202, thus the smoke atomized by the atomizer assembly 203 can directly flow to the suction end 201 without passing the liquid container 202, and the smoke will not be condensed when passing through the liquid container 202, thereby avoiding blocking the smoke channel 501.

In the second arrangement of the air inlet, the air inlet may also be provided on the outer wall of the atomizer assembly 203, and the specific position and number of the air inlet are not limited here.

Figure 11:
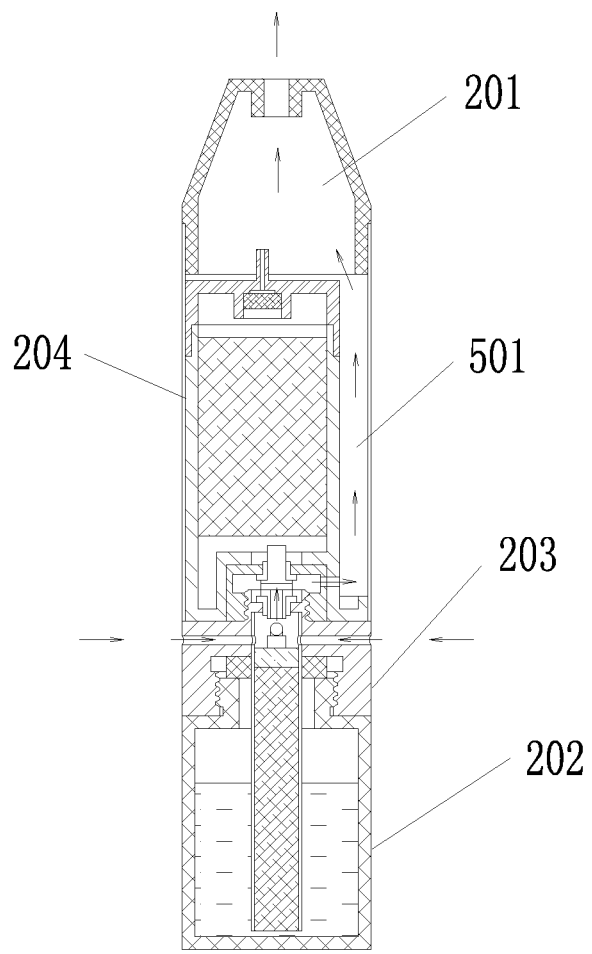
FIG. 11 is a sectional view showing the structure of another preferred embodiment of the electronic cigarette according to the present application.

The suction end 201 may be communicated with the air inlet via the smoke channel 501, which can be referred to FIG. 11. FIG. 11 is a sectional schematic view of the electronic cigarette, in which the air inlet is disposed on the outer wall of the atomizer assembly 203.

As shown in FIG. 11, the air inlet arranged on the outer wall of the atomizer assembly 203 is communicated with the suction end 201 via the smoke channel 501.

In this embodiment, the direction of the air flow in the electronic cigarette is indicated by arrows, and as shown in FIG. 11, the air flow does not pass through the liquid container 202, thus the smoke atomized by the atomizer assembly 203 can directly flow to the suction end 201 without passing the liquid container 202, and the smoke will not be condensed when passing through the liquid container 202, thereby avoiding blocking the smoke channel 501, and avoiding a situation in the conventional technology that, the smoke is condensed when passing through the liquid storing area and further blocks the atomizing channel.

Further, the battery rod assembly 204 according to this embodiment is configured to control the heating wire assembly 301 to atomize the cigarette liquid. Two specific control manners are described as follows.

In the first manner shown in FIG. 9, an air flow sensor 507 for generating a pulse signal is arranged inside the battery casing 502 at a position close to the suction end 201.

The air flow sensor 507 may generate a pulse signal when detecting that the pressure in the smoke channel 501 is reduced, and the pressure reduction indicates that a user is smoking.

Further, in this embodiment, since the air flow sensor 507 is close to the suction end 201, the sensitivity of the air flow sensor 507 for sensing the smoking action of the user is improved, which allows the user to effectively use the electronic cigarette.

A microcontroller for generating a control signal according to the pulse signal is connected to the air flow sensor 507 and the battery 503. Further, the microcontroller is connected to the heating wire assembly 301, to allow the heating wire assembly 301 to atomize the cigarette liquid according to the control signal.

The above arrangement may imitate the smoking process of a real cigarette, and the user may smoke the atomized cigarette liquid via the suction end 201.

Figure 12:
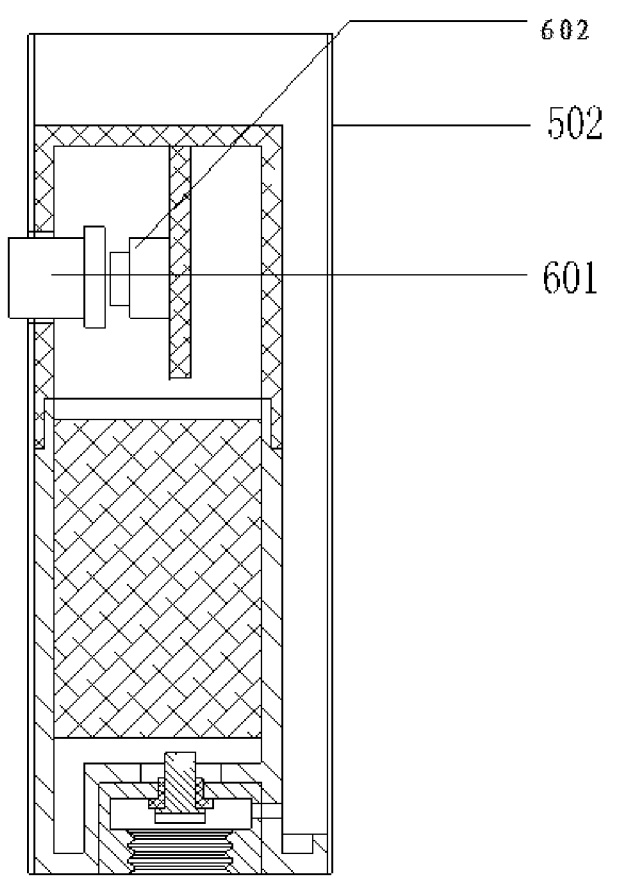
FIG. 12 is another sectional view showing the structure of the battery rod assembly of the electronic cigarette according to the present application.

The second arrangement is shown in FIG. 12.

A push button 601 is provided on the battery casing 502 to receive an operation instruction of the user.

A soft touch switch 602 is connected to the push button 601 and is configured to generate a control signal according to the operation instruction.

The soft touch switch 602 is connected to the heating wire assembly 301, to enable the heating wire assembly 301 to atomize the cigarette liquid according to the control signal.

By using the above arrangement, the heating wire assembly 301 of the electronic cigarette may start to atomize the cigarette liquid once the user presses the push bottom 601, without requiring the user to suck the suction end 201.

Figure 13:
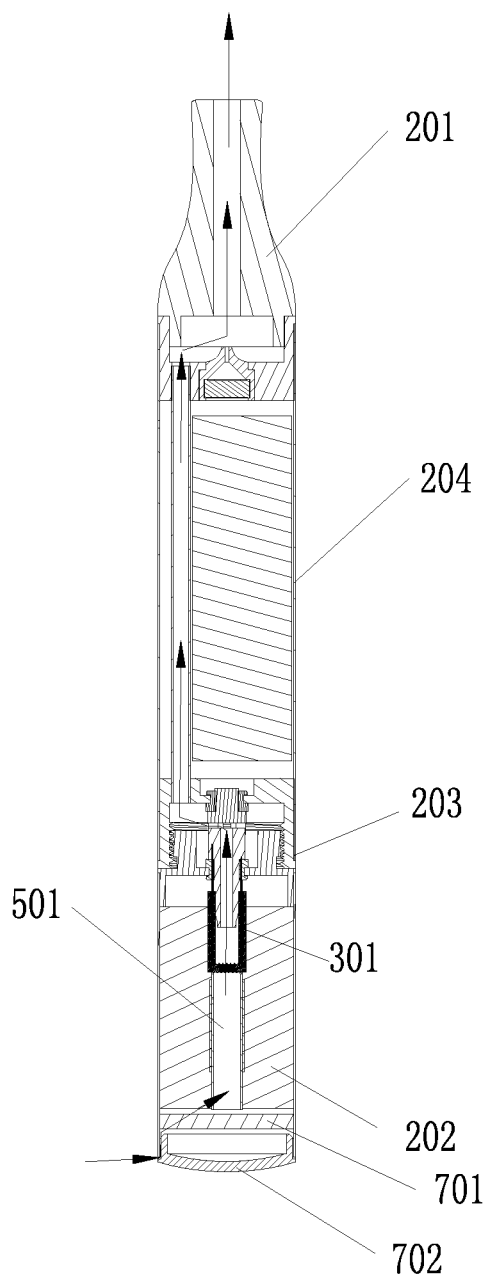
FIG. 13 is a sectional view showing the structure of another preferred embodiment of the electronic cigarette according to the present application.

The electronic cigarette according to the embodiments of the present application may also imitate the real smoking by using light effect. The specific structure is shown in FIG. 13. The electronic cigarette shown in FIG. 13 includes a suction end 201 and a battery rod assembly 204. The specific structures of the suction end 201 and the battery rod assembly 204 can be referred to the above embodiments, which will not be described here.

In this embodiment, the liquid container 202 and the atomizer assembly 203 may be integrally formed, and the liquid container 202 is arranged on the main body of the electronic cigarette at an end away from the suction end 201.

Preferably, a smoke channel 501 is provided inside the liquid container 202, and an air inlet in communication with the smoke channel 501 is provided at a bottom of the liquid container 202. The smoke channel 501 extends along the liquid container 202 until reaching the suction end 201.

The direction of the air flow is indicated by arrows in FIG. 13. As shown in FIG. 13, the smoke channel 501 in this embodiment is longer than the smoke channel in the previous embodiment, and the longer smoke channel 501 may decrease the temperature of the smoke atomized by the heating wire assembly 301, thereby ensuring the smoking experience of the user.

More preferably, a lighting module 701 may be arranged at the bottom of the main body of the electronic cigarette. When the user smokes via the suction end 201, the lighting module 701 may emit light, which can imitate the burning effect of tobacco. Apparently, various light effects can be designed according to requirements of the user.

An end cap 702 for receiving the lighting module 701 is arranged at the bottom of the main body of the electronic cigarette. The end cap 702 may be a transparent case or a non-transparent casing.

Figure 14:
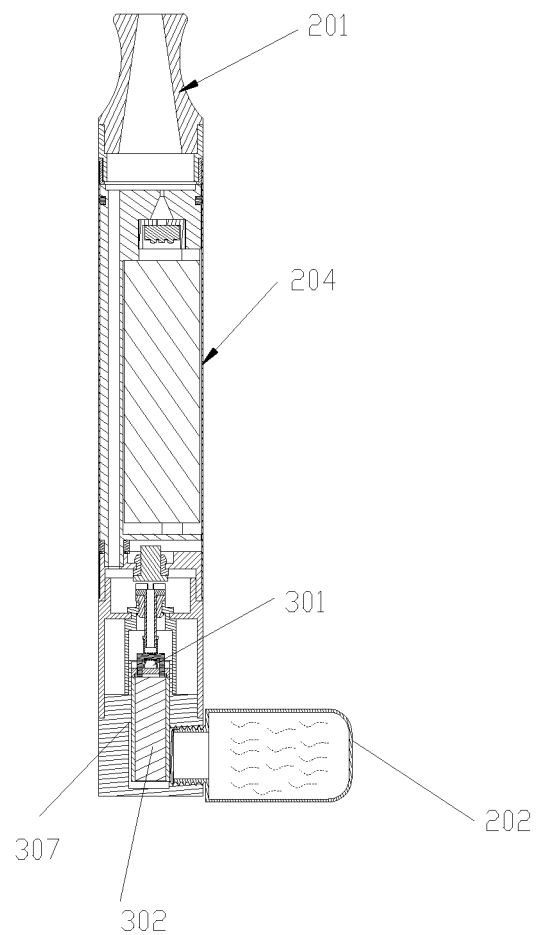
FIG. 14 is a sectional view showing the structure of another preferred embodiment of the electronic cigarette according to the present application.

In order to facilitate delivering the cigarette liquid in the liquid container to the liquid-guiding mechanism, another structure of the electronic cigarette is described in detail in conjunction with the embodiment shown in FIG. 14.

As shown in FIG. 14, the electronic cigarette includes a suction end 201 and a battery rod assembly 204. The specific structures of the suction end 201 and the battery rod assembly 204 can be referred to the above embodiments, which will not be described in detail in this embodiment.

In this embodiment, the liquid container 202 for containing the cigarette liquid is arranged on the outer circumferential wall of the atomizing assembly 203, thus the cigarette liquid in the liquid container 202 can be delivered to the liquid-guiding mechanism 302 in the atomizing sleeve 307 via a liquid hole arranged on the atomizing sleeve 307, which allows the cigarette liquid to be atomized by the heating wire assembly 301. The specific structure inside the atomizing assembly 203 can be referred to the above embodiments, which is not limited in this embodiment.

In this embodiment, the flow direction of the cigarette liquid in the liquid container 202 and the flow direction of the cigarette liquid in the atomizing sleeve 307 which is delivered to the heating wire assembly 301 to be atomized are perpendicular to each other or forms a certain angle with respect to each other, so as to avoid the cigarette liquid being overly delivered to the atomizer due to vibration or other reasons. Thus, the cigarette liquid in the liquid container 202 can be delivered to the liquid-guiding mechanism 302 in the atomizing sleeve 307 smoothly, which ensures a stable output amount of the smoke. In addition, in the case that the electronic cigarette is dropped and hits the ground with its end, this structure can protect the glass liquid container 202 from being broken due to the impact.

In this embodiment, the liquid container 202 is threadedly connected to the atomizer assembly 203, and other connecting manners such as a snap fit may also be used. The specific connecting manner is not limited in this embodiment.

It is to be noted that, in this embodiment, the number and specific position of the liquid container 202 arranged on the side wall of the atomizer assembly 203 are not limited.

For example, as shown in FIG. 14, when only one liquid container 202 is arranged on the side wall of the atomizing assembly 203, the main body of the electronic cigarette presents an L shape.

Figure 15:
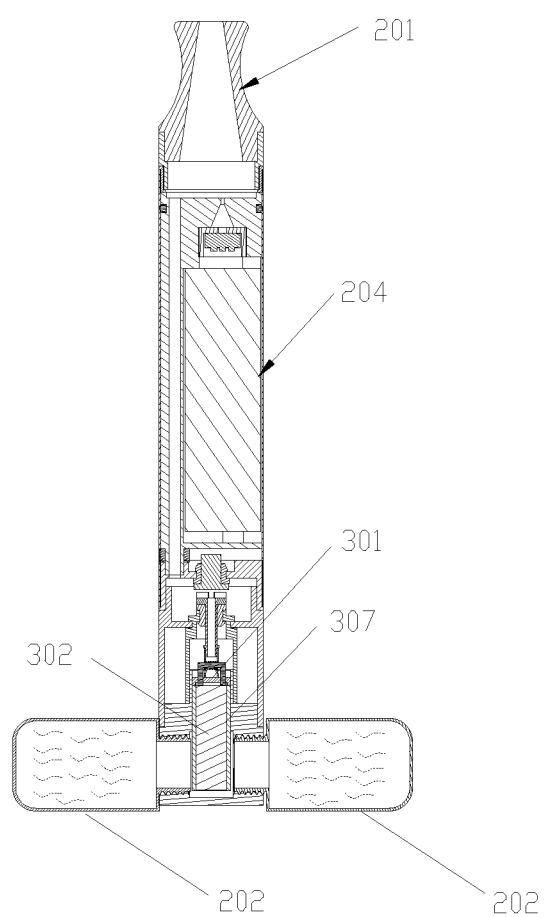
FIG. 15 is a sectional view showing the structure of another preferred embodiment of the electronic cigarette according to the present application.

Or, as shown in FIG. 15, when two liquid containers 202 are opposingly arranged on the side wall of the atomizing assembly 203, the main body of the electronic cigarette presents a T shape.

The technical solutions of the embodiments of the present application are described clearly and completely hereinafter in conjunction with the drawings of the embodiments of the present application. Apparently, the described embodiments are only a few of the embodiments of the present application, rather than all embodiments. All of other embodiments, made by those skilled in the art based on the embodiments in the present application without any creative efforts, are deemed to fall into the scope of the present application.

The above embodiments are described in a progressive manner. Each of the embodiments is mainly focused on describing its differences from other embodiments, and references can be made among these embodiments for the same or similar portions.

Based on the above description of the disclosed embodiments, the person skilled in the art is capable of carrying out or using the present application. It is obvious for the person skilled in the art to make many modifications to these embodiments. The general principle defined herein may be realized in other embodiments without departing from the spirit or scope of the present application. Therefore, the present application is not limited to the embodiments illustrated herein, but should be defined by the broadest scope consistent with the principle and novel features disclosed herein.

The invention claimed is:

1. An electronic cigarette, comprising:
a main body of the electronic cigarette;
wherein, a functional element, a protection mechanism and a magnetic locating member are provided on the main body of the electronic cigarette;
the protection mechanism is slidably connected to the main body of the electronic cigarette and is configured to cover the functional element; and
the magnetic locating member is connected to the protection mechanism magnetically, and is configured to prevent the protection mechanism from randomly sliding on the main body of the electronic cigarette in a case that the functional element is exposed or covered by the protection mechanism; and
the protection mechanism has two ends, the two ends of the protection mechanism are both provided with a retainer; and
the magnetic locating member is arranged between the retainers, and is configured to abut against the retainers to limit a sliding distance of the protection mechanism and prevent the protection mechanism from falling off the main body of the electronic cigarette.

2. The electronic cigarette according to claim 1, wherein, the protection mechanism is a sleeve which is sleeved on the main body of the electronic cigarette;
each of the retainers is a retaining ring protruding out of an inner surface of the sleeve;
the magnetic locating member is a connecting ring; and
the connecting ring is arranged between the retainers and is configured to abut against the retaining rings to limit a sliding distance of the sleeve.

3. The electronic cigarette according to claim 2, wherein the connecting ring is provided with at least two slide grooves;
the sleeve is provided with slide rails which are configured to cooperate with the slide grooves and are slidable axially with respect to the main body of the electronic cigarette;
the retaining rings are arranged at two ends of the slide rails; and
the slide rails are arranged in an axial direction of the main body of the electronic cigarette.

4. The electronic cigarette according to claim 3, wherein, each of the retaining rings is a magnet, and the connecting ring is made of ferrous materials;
or,
each of the retaining rings is made of ferrous materials, and the connecting ring is a magnet.

5. The electronic cigarette according to claim 1, wherein, the protection mechanism is provided with an opening configured to allow a user to use the functional element;
the protection mechanism is provided with at least two circumferential grooves along a circumferential direction of the main body of the electronic cigarette;
the magnetic locating member is provided with circumferential protrusions configured to cooperate with the circumferential grooves; and
the protection mechanism is slidable in the circumferential direction of the main body of the electronic cigarette through the cooperation between the circumferential grooves and the circumferential protrusions.

6. The electronic cigarette according to claim 5, wherein,
the protection mechanism is further provided with first retaining strips arranged at two sides of the opening in an axial direction of the main body of the electronic cigarette; and
the main body of the electronic cigarette is further provided with a second retaining strip for cooperating with the first retaining strips, and the second retaining strip is configured to abut against the first retaining strips to limit a sliding range of the protection mechanism.

7. The electronic cigarette according to claim 6, wherein,
each of the first retaining strips is a magnet, and the second retaining strip is made of ferrous materials;
or,
each of the first retaining strips is made of ferrous materials, and the second retaining strip is a magnet.

8. The electronic cigarette according to claim 1, wherein, the functional element comprises a push button and/or a display.

9. The electronic cigarette according to claim 1, wherein, the main body of the electronic cigarette is further provided with a suction end, a liquid container for containing cigarette liquid, an atomizer assembly for atomizing the cigarette liquid, and a battery rod assembly for supplying power to the atomizer assembly;
the liquid container is arranged on the main body of the electronic cigarette at an end away from the suction end; and
wherein the atomizer assembly comprises a heating wire assembly and a liquid-guiding mechanism.

10. The electronic cigarette according to claim 9, wherein, the atomizer assembly is arranged between the battery rod assembly and the liquid container, and the suction end is arranged at an outer side of an end of the battery rod assembly, in a middle of the battery rod assembly, or on the battery rod assembly at a position away from the atomizer assembly.

11. The electronic cigarette according to claim 9, wherein, the liquid container is detachably connected to the atomizer assembly;
and/or,
the atomizer assembly is detachably connected to the battery rod assembly.

12. The electronic cigarette according to claim 9, wherein, the atomizer assembly and the battery rod assembly are arranged coaxially.

13. The electronic cigarette according to claim 9, wherein, the atomizer assembly further comprises:
an atomizer bracket;
a first thread bushing arranged at a top of the atomizer bracket and configured to be detachably connected to the battery rod assembly;
an atomizer electrode fixedly arranged inside the first thread bushing and electrically connected to the heating wire assembly;
an insulating ring arranged between the first thread bushing and the atomizer electrode; and
an atomizing sleeve arranged on the atomizer bracket, and the liquid-guiding mechanism is arranged inside the atomizing sleeve.

14. The electronic cigarette according to claim 11, wherein,
a smoke channel for communicating the suction end with an air inlet is provided inside the battery rod assembly; and
the air inlet is arranged on an abutting surface of the atomizer assembly and the liquid container; or,
the air inlet is arranged on an outer wall of the atomizer assembly.

15. The electronic cigarette according to claim 13, wherein, the battery rod assembly comprises:
a battery casing;
a battery disposed inside the battery casing;
a battery bracket provided inside the battery casing to fix the battery;
a battery electrode arranged at an end of the battery bracket and electrically connected to the battery and the atomizer electrode; and
a second thread bushing for cooperating with the first thread bushing to allow the battery rod assembly to be detachably connected to the atomizer assembly.

16. The electronic cigarette according to claim 13, wherein,
a sealing ring for sealing the liquid container is provided at a connection portion between the atomizer bracket and the liquid container.

17. The electronic cigarette according to claim 9, wherein,
an annular sealing plug with a through hole is provided to sealingly cooperate with an opening of the liquid container; and
a pierceable membrane for sealing the liquid container is arranged inside the through hole of the annular sealing plug.

18. The electronic cigarette according to claim 1, wherein, a non-metallic elastic member is connected to each of the retainers and is configured to elastically abut against a surface of the main body of the electronic cigarette, or each of the retainers is a non-metallic member.

* * * * *